(12) United States Patent
Kaharu

(10) Patent No.: US 7,780,956 B2
(45) Date of Patent: Aug. 24, 2010

(54) HAIR COSMETIC

(75) Inventor: Takeshi Kaharu, Tokyo (JP)

(73) Assignee: Kao Corporation, Tokyo (JP)

( * ) Notice: Subject to any disclaimer, the term of this patent is extended or adjusted under 35 U.S.C. 154(b) by 50 days.

(21) Appl. No.: 11/911,011

(22) PCT Filed: Apr. 10, 2006

(86) PCT No.: PCT/JP2006/307992

§ 371 (c)(1),
(2), (4) Date: Apr. 1, 2008

(87) PCT Pub. No.: WO2006/109877

PCT Pub. Date: Oct. 19, 2006

(65) Prior Publication Data

US 2009/0068134 A1    Mar. 12, 2009

(30) Foreign Application Priority Data

Apr. 11, 2005   (JP) .............................. 2005-113692

(51) Int. Cl.
*A61Q 5/12* (2006.01)

(52) U.S. Cl. ................. 424/70.27; 424/70.31

(58) Field of Classification Search ........................ None
See application file for complete search history.

(56) References Cited

U.S. PATENT DOCUMENTS

| | | | |
|---|---|---|---|
| 5,776,443 A | | 7/1998 | Vinski et al. |
| 2003/0012761 A1* | | 1/2003 | Yoshida et al. ............ 424/70.17 |
| 2004/0096412 A1* | | 5/2004 | Uehara et al. ............. 424/70.12 |
| 2005/0232893 A1 | | 10/2005 | Kaharu et al. |

FOREIGN PATENT DOCUMENTS

| JP | 55-33745 | 3/1980 |
|---|---|---|
| JP | 4-279512 | 10/1992 |
| JP | 5-271035 | 10/1993 |
| JP | 5 271035 | 10/1993 |
| JP | 5-271036 | 10/1993 |
| JP | 7-61911 | 3/1995 |
| JP | 7 61911 | 3/1995 |
| JP | 8-157332 | 6/1996 |
| JP | 10-72324 | 3/1998 |
| JP | 11-79947 | 3/1999 |
| JP | 11 79947 | 3/1999 |
| JP | 2998027 | 1/2000 |
| JP | 2000-86454 | 3/2000 |
| JP | 2002-114648 * | 4/2002 |
| JP | A 2002-338438 | 11/2002 |
| JP | 2003 26548 | 1/2003 |
| JP | 2003-26548 | 1/2003 |
| JP | 2003 113046 | 4/2003 |
| JP | 2004-002261 * | 1/2004 |
| JP | 2004 10580 | 1/2004 |
| JP | 2004-10580 | 1/2004 |
| JP | 2003-113046 | 4/2004 |
| JP | 2004 292390 | 10/2004 |
| JP | 2004-292390 | 10/2004 |
| JP | 2005-053823 * | 3/2005 |
| WO | 2004-030646 | 4/2004 |

OTHER PUBLICATIONS

Fragrance Journal, vol. 24, No. 12, pp. 106-111, 1996 (with English abstract).

* cited by examiner

*Primary Examiner*—Robert A Wax
*Assistant Examiner*—Bethany Barham
(74) *Attorney, Agent, or Firm*—Oblon, Spivak, McClelland, Maier & Neustadt, L.L.P.

(57) ABSTRACT

The present invention provides hair cosmetics containing (a) an amideamine (I):

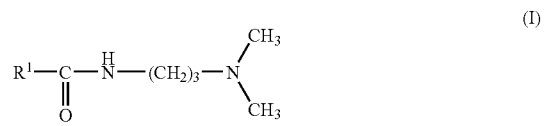

wherein $R^1CO$ represents fatty acid residues among which $C_{20}$ or more fatty acid residues account for 60 percent by weight or more, $C_{20}$ fatty acid residues account for 3 percent by weight or more, and $C_{22}$ fatty acid residues account for 50 to 95 percent by weight; (b) an organic acid; and (c) a C8 to C30 aliphatic alcohol, wherein the content of the component (b) is 1.5 to times as many moles as the amine equivalent of the component (a).

20 Claims, No Drawings

HAIR COSMETIC

FIELD OF THE INVENTION

The present invention relates to hair cosmetics containing an amideamine.

BACKGROUND OF THE INVENTION

Hair cosmetics such as a rinse, conditioner, treatment, etc. are used for improving the feel of hair after shampooing. These hair cosmetics contain a quaternary ammonium salt as a main component to improve the feel of hair, and are used mainly in the form of a gelled emulsion by further incorporation of an aliphatic alcohol such as cetanol or an oil to improve efficacy feeling. However, these hair cosmetics cannot be said to provide a sufficient smooth feel and moist feel to hair.

It was found in recent years that a specific amideamine compound or its acid salt can confer smooth feel and softness on hair, and hair cosmetics containing the amideamine compound or its acid salt have been proposed (see, for example, JP-A 5-271035, JP-A 5-271036 and WO-A 2004/030646).

The amideamine compound or its salt is also known to provide hair cosmetics which are highly safe and show a mild action on skin etc. (see FRAGRANCE JOURNAL, 24(12), 106-111 (1996)). Further, stearic acid dimethylaminopropylamide is known as a specific amideamine.

In recent years, it has become common to enjoy changing the appearance of hair freely such as changing hair color (coloring) and changing hair style (permanent waving), and damage to hair such as a dry and frictional feel and entanglement, attributable to such practice, has been drawing attention. It is estimated that damage to hair by coloring treatment or permanent waving treatment is caused by chemical factors forming cavities in the hair with a hair dye or permanent waving agent used for the treatment. It is also said that damage to hair, such as the absence of luster, a dry and frictional feel, etc. is caused by the formation of cavities in the hair by physical factors such as heating with a dryer for drying hair after shampooing.

For repairing the damaged hair, hair cosmetics containing water-insoluble cationic fine particles (JP-A 10-72324) and hair cosmetics containing an amino acid-based amphoteric surfactant and a naturally occurring triglyceride to repair hair (JP-A 2000-86454) have been proposed. For preventing damage, hair cosmetics containing phytantriol and silicone (U.S. Pat. No. 5,776,443), hair cosmetics containing dimethyl silicone gum, polyethylene glycol and a cationic surfactant (JP-A 4-279512), and hair cosmetics containing hydrolyzed wheat proteins, wheat oligosaccharides, wheat amino acids and panthenol (JP-A 8-157332) have been proposed.

For improving optical properties such as hair luster, various hair cosmetics containing components such as an organopolysiloxane oxyalkylene copolymer and acrylic resin have been proposed (JP-A 55-33745).

Hair cosmetics using a cationic surfactant etc. in combination with a polyhydric alcohol, hydroxypropyl cellulose etc. to confer luster on hair are also proposed (JP-B 2998027).

Any conventional methods of repairing hair are those making hair repair felt temporarily by repairing the cuticle edge on the surface of hair or by adsorbing an oil onto the surface of hair, but not those capable of repairing or preventing cavities in the hair, which are an essential cause for damage.

Also, JP-A 55-33745 supra is to improve optical properties by allowing the hair cosmetics to act on the surface of hair or on cuticles in the vicinity thereof, and its effect is temporary and insufficient. JP-B 2998027 also has problems in feeling upon use by application to hair, for example in smoothness, etc.

Further, compositions when blended with other components such as an aliphatic alcohol or an oil are problematic in stability, for example in gel formability, and cannot be satisfactory in smoothness and moist feel to be conferred on hair.

SUMMARY OF THE INVENTION

The present invention provides hair cosmetics containing the following components (a), (b) and (c):

(a) an amideamine represented by the general formula (I) (referred to hereinafter as amideamine (I)):

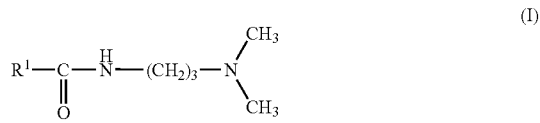

wherein $R^1CO$ represents fatty acid residues among which C20 or more fatty acid residues account for 60 percent by weight or more, C20 fatty acid residues account for 3 percent by weight or more, and C22 fatty acid residues account for 50 to 95 percent by weight, (b) an organic acid, and (c) a C8 to C30 aliphatic alcohol, wherein the content of the component (b) is 1.5 to 10 times as many moles as the amine equivalent of the component (a).

DETAILED DESCRIPTION OF THE INVENTION

The present inventor has found that by using a specific amount of an organic acid relative to an amideamine having a hydrocarbon chain of specific length, and further by using an aliphatic alcohol in combination therewith, hair damaged by coloring and drying with a dryer can be repaired and prevented, while a sufficiently smooth coating feel can be provided during shampooing and rinsing after application to hair, and a smooth finish and manageable feel can be conferred even on damaged hair.

The present invention provides hair cosmetics which are excellent in an effect of repairing and preventing hair damage (cavities in the hair) attributable to coloring and drying with a dryer, can provide a sufficiently smooth coating feel during shampooing and rinsing after application to hair, can confer a smooth finish and manageable feel even on damaged hair, are highly safe, and exhibit a moderate action on skin, etc.

The hair cosmetics of the present invention are excellent in the effect of repairing and preventing hair damage (cavities in the hair) attributable to coloring and drying with a dryer, can provide a sufficiently smooth coating feel during shampooing and rinsing after application to hair, and can confer a smooth and manageable finish feel even on damaged hair.

In the amideamine (I) as the component (a) used in the present invention, the fatty acid residues represented by $R^1CO$ contain 60 percent by weight or more of fatty acid residues having at least 20 carbon atoms, 3 percent by weight or more of fatty acid residues having 20 carbon atoms, and 50 to 95 percent by weight of fatty acid residues having 22 carbon atoms, each amount being relative to the total fatty acid residues.

From the standpoint of providing good softness and smoothness during wet state and even after drying, especially an excellent smoothness after drying, the fatty acid residues preferably contain 75 percent by weight or more, more preferably 90 percent by weight or more of fatty acid residues having at least 20 carbon atoms; 4 percent by weight or more, more preferably 5 percent by weight or more of fatty acid residues having 20 carbon atoms; and 55 to 95 percent by weight, more preferably 70 to 95 percent by weight, even more preferably 80 to 95 percent by weight of fatty acid residues having 22 carbon atoms.

In the present invention, the fatty acid residues mean the group of $R^1CO$—.

From the viewpoint of conferring a smooth and soft feeling during application through rinsing and drying and of the stability of the system, the content of the component (a) in the hair cosmetics of the present invention is preferably 0.1 to 10 percent by weight, more preferably 0.1 to 5 percent by weight, even more preferably 0.5 to 3 percent by weight.

The organic acid as the component (b) in the present invention is preferably an organic acid having 10 or less carbon atoms. Examples of the organic acid include acids having a C10 or less short chain alkyl group, such as alkylphosphoric acids, alkylsulfonic acids and alkylsulfuric acids; monocarboxylic acids such as acetic acid and propionic acid; dicarboxylic acids such as malonic acid, succinic acid, glutaric acid, adipic acid, maleic acid, fumaric acid and phthalic acid; polycarboxylic acids such as polyglutamic acid; acidic amino acids such as L-glutamic acid and L-aspartic acid; pyroglutamic acid; aromatic acids such as benzoic acid and p-toluenesulfonic acid; and hydroxycarboxylic acids such as glycolic acid, lactic acid, glyceric acid, gluconic acid, pantothenic acid, malic acid, tartaric acid and citric acid. From the viewpoint of bringing about a moistening and softening effect on hair and further in respect of an effect of repairing and preventing hair damage (cavities in the hair) attributable to coloring, permanent waving treatment, drying with a dryer, etc., dicarboxylic acids, acidic amino acids, pyroglutamic acid and hydroxycarboxylic acids are preferable, among which hydroxycarboxylic acids and dicarboxylic acids are more preferable. The organic acids can also be used as a mixture of two or more thereof.

The content of the component (b) in the hair cosmetics of the present invention is 1.5 to 10 times, preferably 1.5 to 6 times, as many moles as the amine equivalent of the component (a). In the present invention, an organic acid salt of the amideamine (I) may be previously formed from the amideamine (I) as component (a) and the organic acid as component (b) and then incorporated in the hair cosmetics.

The hair cosmetics of the present invention contains an aliphatic alcohol having 8 to 30 carbon atoms as the component (c), which is preferably an aliphatic alcohol having a linear alkyl or alkenyl group or a branched alkyl group, having 8 to 26 carbon atoms, more preferably 10 to 26 carbon atoms. Linear alcohols having 10 to 26 carbon atoms are more preferable. Examples thereof include cetyl alcohol, stearyl alcohol, arachyl alcohol and behenyl alcohol, among which stearyl alcohol is more preferable. From the viewpoint of finger combing and smoothness upon application to hair, the ratio of linear alcohol is preferably 80% or more. When this ratio is 80% or more, the hair cosmetics are excellent in thickening property (gel formability) to attain an excellent application performance.

These components (c) may be a combination of two or more thereof, and the content of the components (c) in the hair cosmetics of the present invention is preferably 0.1 to 20 percent by weight, more preferably 0.1 to 15 percent by weight, even more preferably 0.5 to 10 percent by weight, from the viewpoint of smoothness upon application, rinsing, and after drying as well as the stability of the system.

The pH of the hair cosmetics of the invention for application to hair (that is, the pH of the hair cosmetics in the form of 5 percent by weight aqueous solution at 25° C.) is preferably 2 to 8 from the viewpoint of good feel of hair and stability of the product, more preferably 2.5 to 6, even more preferably 2.5 to 4.5, from the viewpoint of an effect of repairing and preventing hair damage (cavities in the hair) attributable to coloring, permanent waving treatment, drying with a dryer, etc. As a pH adjuster, not only the component described as organic acid but bases such as sodium hydroxide, potassium hydroxide and ammonium chloride can also be used.

The present invention may further contain an ether amine represented by the general formula (XI) (hereinafter referred to as ether amine (XI)):

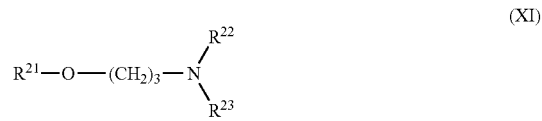

(XI)

wherein $R^{21}$ is a linear or branched $C_6$ to $C_{24}$ alkyl or alkenyl group, $R^{22}$ and $R^{23}$ are the same or different and each independently represents a C1 to C6 alkyl group, or a group -$(AO)_mH$ in which A represents a C2 to C4 alkylene group, m is a number of 1 to 6, and the group A in number of m may be the same or different and may be arranged in any order.

In the ether amine (XI) used in the present invention, $R^{21}$ is a linear or branched $C_6$ to $C_{24}$ alkyl or alkenyl group. A linear or branched $C_{12}$ to $C_{24}$ alkyl or alkenyl group, preferably $C_{14}$ to $C_{22}$ alkyl or alkenyl group, more preferably alkyl group is preferred because it can provide good softness and smoothness to the hair from wetting to even after drying, to make the hair excellent in smoothness after drying.

$R^{22}$ and $R^{23}$ each independently represents a C1 to C6 alkyl group, or a group -$(AO)_mH$ (in which A and m have the same meanings as described above). A C1 to C6 alkyl group or a group —$(CH_2CH_2O)_nH$ (in which n stands for a number from 1 to 3, preferably 1), preferably a C1 to C6 alkyl group, more preferably a methyl or ethyl group is preferred because it can provide good softness and smoothness to the hair during wet state and even after drying, to make the hair excellent in smoothness after drying.

In the hair cosmetics of the present invention, the total content of the ether amine (XI) and the component (a) is preferably 0.01 to 20 percent by weight, more preferably 0.1 to 15 percent by weight, even more preferably 0.1 to 10 percent by weight from the viewpoint of providing a good feeling to the hair as well as the stability of the product. The content of each of the ether amine (XI) and the component (a) in the hair cosmetics of the present invention is preferably 0.1 to 10 percent by weight, more preferably 0.1 to 5 percent by weight, even more preferably 0.5 to 3 percent by weight.

The weight ratio of the component (a) to the ether amine (XI) in the hair cosmetics of the present invention, that is, (a)/(XI) is 10/1 to 1/10, preferably 7/1 to 1/7, from the viewpoint of reducing unpleasant slimy feel and stickiness on the hair or body during treatment.

An organic solvent can be contained in the hair cosmetics of the present invention, from the viewpoint of not only improving smoothness and smooth feel during application/rinsing but also conferring softness on the hair after drying and from the viewpoint of conferring an action of accelerating the penetration of the organic acid as component (b) into the hair.

The organic solvent includes an organic solvent selected from the following (d1) to (d5):

(d1) Compounds represented by the general formula (II):

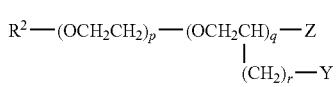

wherein $R^2$ represents a hydrogen atom, an alkyl group having from 1 to 6 carbon atoms or a group $R^3$-Ph-$R^4$— (in which $R^3$ represents a hydrogen atom, a methyl group or a methoxy group, $R^4$ represents a direct bond or a saturated or unsaturated divalent hydrocarbon group having from 1 to 3 carbon atoms, and Ph represents a paraphenylene group), Y and Z each represents a hydrogen atom or a hydroxyl group, p, q and r each represents an integer of from 0 to 5, with the proviso that when p=q=0, Z represents a hydroxyl group, and $R^2$ represents neither a hydrogen atom nor a group $R^3$-Ph-.

(d2) N-Alkylpyrrolidones having a $C_{1-18}$ alkyl group bound to a nitrogen atom.

(d3) Alkylene carbonates whose alkylene group has 2 to 4 carbon atoms.

(d4) Propylene glycols having a molecular weight of from 200 to 5000.

(d5) Lactones or cyclic ketones represented by the general formula (III), (IV) or (V):

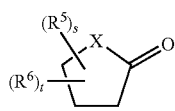

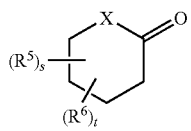

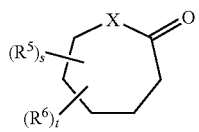

wherein X represents a methylene group or an oxygen atom, $R^5$ and $R^6$ represent substituents which are different from each other, and s and t each represents 0 or 1.

When p=q=0 and Z represents a hydroxyl group, examples of (d1) include monohydric alcohols such as ethanol, 1-propanol, 2-propanol, butanol and isobutanol. Examples of (d1) having a group $R^3$-Ph-$R^4$— include aromatic alcohols such as benzyl alcohol, cinnamyl alcohol, phenethyl alcohol, p-anisyl alcohol, p-methylbenzyl alcohol, phenoxyethanol and 2-benzyloxyethanol. Additional examples include polyhydric alcohols such as ethylene glycol, propylene glycol, 1,3-butanediol and glycerin, and methyl carbitol, ethyl carbitol, propyl carbitol, butyl carbitol, triethylene glycol monoethyl ether and triethylene glycol monobutyl ether.

Examples of (d2) include N-methylpyrrolidone, N-octylpyrrolidone and N-laurylpyrrolidone.

Examples of (d3) include ethylene carbonate and propylene carbonate.

The polypropylene glycol (d4) preferably has a molecular weight of from 200 to 1000.

Each of $R^5$ and $R^6$ in (d5) represented by the formulae (III) to (V) is preferably a linear, branched or cyclic alkyl group, hydroxyl group, sulfonic acid group, phosphoric acid group, carboxyl group, phenyl group, sulfoalkyl group, alkyl phosphate group or carboxyalkyl group. Among them, preferred ones are a C1 to C6 linear or branched alkyl group such as methyl, ethyl, propyl, isopropyl or butyl substituted at the γ-position in the case of γ-lactone or at the δ-position (that is, methylene adjacent to the hetero oxygen atom) in the case of δ-lactone. For enhancing the water solubility of the compounds represented by the formulae (III) to (V), preferred $R^5$ and $R^6$ are an acidic group such as sulfonic acid group, phosphoric acid group or carboxyl group or an alkyl group substituted therewith. As (d5), examples of the lactone include γ-butyrolactone, γ-caprolactone, γ-valerolactone, δ-valerolactone, δ-caprolactone, and δ-heptanolactone. From the viewpoint of stability of lactone, preferred is γ-lactone, more preferably γ-butyrolactone and γ-caprolactone. Examples of the cyclic ketone as (d5) include cyclopentanone, cyclohexanone, cycloheptanone and 4-methylcycloheptanone.

Of these organic solvents, aromatic alcohols and polyhydric alcohols as (d1), alkylene carbonates as (d3) and polypropylene glycol as (d4) are preferred. Two or more of these organic solvents may be used in combination.

The content of the organic solvent in the hair cosmetics of the present invention is preferably from 0.1 to 20 percent by weight, more preferably from 0.1 to 10 percent by weight, from the viewpoint of absorptivity of the agent on the hair and conferring elasticity to the hair.

The hair cosmetics of the present invention can further contain an oily component other than the component (c), in order to improve hair protecting effects such as conferring luster, smoothness and flexibility after drying. The oily component includes not only silicones and ester oils, but also higher fatty acids such as capric acid, lauric acid, myristic acid, palmitic acid, stearic acid, behenic acid, oleic acid, coconut oil fatty acid, isostearic acid and isopalmitic acid, and hydrocarbon oils such as liquid paraffin, liquid isoparaffin, vaseline, squalene and squalane.

The silicones include silicone rubber, silicone oil, functional group-modified silicone, etc. For example, silicones in the following (i) to (viii) can be exemplified.

(i) Highly Polymerized Dimethyl Polysiloxane;

The highly polymerized dimethyl polysiloxane can usually be used in the form of a dilution in a liquid oil (for example, liquid silicone oil such as the following dimethyl polysiloxane oil and cyclic silicone, or liquid hydrocarbon oil such as isoparaffin) or emulsion.

Specific examples include BY22-019, FZ-4188, BY11-026, BY11-040 and FZ-3174 (manufactured by Dow Corning Toray Silicone Co., Ltd.).

(ii) Dimethyl Polysiloxane Oil Represented by the Formula (VI):

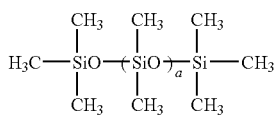
(VI)

wherein a stands for an integer of from 0 to 650.

Specific examples include commercially available products such as SH200C series with viscosities of 1 cs, 50 cs, 200 cs, 1000 cs, 5000 cs (manufactured by Dow Corning Toray Silicone Co., Ltd.).

(iii) Cyclic Silicone Represented by the Formula (VII);

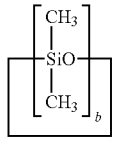
(VII)

wherein b stands for an integer of from 3 to 7.

Specific examples include octamethylcyclotetrasiloxane, decamethylcyclopentasiloxane and dodecamethylcyclohexasiloxane. Examples of the commercially available product include SH244 and SH245 (manufactured by Dow Corning Toray Silicone Co., Ltd.).

(iv) Amino-Modified Silicone Represented by the Formula (VIII);

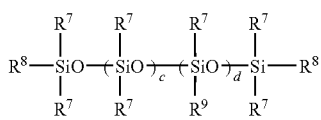
(VIII)

wherein $R^7$ represents a methyl group, $R^8$ represents the same group as that of $R^9$, a methyl group or a hydroxyl group, $R^9$ represents a reactive functional group represented by $—R^{10}—W$ wherein $R^{10}$ represents a C3 to C6 divalent hydrocarbon group, and W represents a primary to tertiary amino-containing group or an ammonium-containing group, and c and d each represents a positive number, c+d is a number depending on the molecular weight, and the average molecular weight is preferably 3000 to 100000.

Specific examples include SS-3551, SF8452C, DC8500 and DC929 (all available from Dow Corning Toray Silicone Co., Ltd.) and KT 1989 (available from GE Toshiba Silicone Co., Ltd.). When the amino-modified silicone is used in the form of an aqueous emulsion, the amount of the amino-modified silicone contained in the aqueous emulsion is preferably 20 to 60 percent by weight, more preferably 30 to 50 percent by weight. Preferred examples of the aqueous emulsion of an amino-modified silicone include SM8704C and SM8904C (available from Dow Corning Toray Silicone Co., Ltd.).

(v) Polyether-Modified Silicone;

For example, SH3771M, FZ-2222 and FZ-2231 (all from Dow Corning Toray Silicone Co., Ltd.) etc. can be mentioned.

(vi) Fluorine-modified silicone (vii) Alkyl-modified silicone (viii) Amino-Modified Siloxane/Polyoxyalkylene Block Copolymer The copolymer represented by the formula (IX) is preferable. For example, FZ-3789, SILSTYLE 201, SILSTYLE 401, SILSTYLE 104 (manufactured by Dow Corning Toray Silicone Co., Ltd.) can be mentioned.

(IX)

wherein $R^{11}$ represents a hydrogen atom or a C1 to C6 monovalent hydrocarbon group, $R^{12}$ represents either the same group as that of $R^{11}$ or E, E represents a reactive functional group represented by $—R^{13}$-G wherein $R^{13}$ represents a direct bond or a C1 to C20 divalent hydrocarbon group, and G represents a primary to tertiary amino-containing group or an ammonium-containing group, e represents a number of 2 or more, f represents a number of 1 or more, j represents a number of 2 to 10, j in number of g may be the same or different, g represents a number of 4 or more, h represents a number of 2 or more, and D represents a divalent organic group bound via a carbon-silicone atom to the adjacent silicon atom and bound via an oxygen atom to a polyoxyalkylene block chain, and a plurality of $R^{11}$, $R^{12}$ and E may be the same or different from one another.

Among these silicone compounds, the highly polymerized dimethyl polysiloxane (i), the dimethyl polysiloxane oil (ii), the cyclic silicone (iii), the amino-modified silicone (iv), the amino-modified siloxane/polyoxyalkylene block copolymer (viii), or a mixture thereof is preferable, among which the amino-modified silicone (iv), the amino-modified siloxane/polyoxyalkylene block copolymer (viii) are more preferable.

The silicones may be used as a combination of two or more thereof. The content of the silicones in the hair cosmetics is preferably 0.1 to 20 percent by weight, more preferably 0.5 to 10 percent by weight, even more preferably 1.0 to 5 percent by weight, from the viewpoint of providing an excellent feeling to hair.

Ester oil is preferably a monoester oil, an ester oil having two or more ester bonds in the molecule thereof, fats and oils or a mixture thereof. Examples of such ester oil include camellia oil, Macadamia nut oil, corn oil, olive oil, avocado oil, castor oil, safflower oil, jojoba oil, sunflower oil, rapeseed oil, sesame oil, soybean oil and meadow foam oil; and ester oils such as isopropyl myristate, isopropyl palmitate, myristyl myristate, octyl palmitate, stearyl stearate, isocetyl stearate, isononyl isononanoate, isotridecyl isononanoate, hydrogenated castor oil stearate, hydrogenated castor oil hydroxystearate, glyceryl tri-2-ethylhexanoate, pentaerythritol tetra-2-ethylhexanoate, neopentyl glycol dicaprate, diglyceryl diisostearate and esters between dipentaerythritol and a mixed fatty acid such as hydroxystearic acid/stearic acid/rosic acid. These may be used as a mixture of two or more thereof.

The content of the ester oil is preferably 0.1 to 20 percent by weight, more preferably 0.1 to 5 percent by weight, even more preferably 0.1 to 2 percent by weight, based on the hair cosmetics.

The content of oily components other than the component (c) in the hair cosmetics of the present invention is preferably 0.1 to 20 percent by weight, more preferably 0.1 to 10 percent by weight, even more preferably 0.5 to 5 percent by weight, from the viewpoint of conferring excellent feel on hair. Though depending on balance with other ingredients, an oily component content of 0.1 percent by weight or more provides smoothness and softness during application and rinsing, and gives rise to an excellent feel and combing after drying, while with an oily component of 20 percent by weight or less given, the hair cosmetics do not feel heavy upon use or frictional during rinsing.

The hair cosmetics of the present invention can further be blended with a hair restoration component, a surfactant, water, etc. The hair restoration component is a compound having a hair-restoring effect, and preferable example include amino acids, amino acid derivatives, vitamins, sphingosines, ceramides, etc.

The amino acids include arginine, lysine, histidine, proline, cysteine, methionine, serine, threonine, tyrosine, glutamine, isoleucine, etc. Arginine and lysine are more preferable. The amino acid derivatives include trimethyl glycine, acylated amino acids, acylalkyl amino acids, and peptides such as dipeptides and tripeptides. The amino acid derivatives also include animal-derived proteins such as keratin, elastin, collagen, lactoferrin, casein, α(β)-lactoalbumin, globulins, ovalbumin, etc. or hydrolysates thereof; proteins derived from plants such as wheat, malt, soybean, silk, etc. or hydrolysates thereof; protein obtained from a pearl or a shell having a pearl layer or hydrolysates thereof; and a protein-containing extract obtained from seeds of legume plants. Keratin, elastin, collagen, casein and hydrolysates thereof, wheat protein, soybean protein, silk protein and hydrolysates thereof are more preferable. In the present invention, these amino acids and amino acid derivatives can be used alone or as a mixture of two or more thereof. The content thereof in the total amount of the hair cosmetics of the present invention is 0.01 to 7 percent by weight, more preferably 0.05 to 2 percent by weight.

The vitamins include tocopherol acetate, ascorbic acid, vitamin B1, vitamin B5, vitamin D, vitamin A, nicotinic acid amide, panthenol, pantothenyl ethyl ether, etc., among which tocopherol acetate, panthenol, and pantothenyl ethyl ether are preferable. When the vitamins are contained, the amount of the vitamins compounded is preferably 0.01 to 2 percent by weight, more preferably 0.05 to 1 percent by weight, based on the total amount of the hair cosmetics of the present invention.

The sphingosines include dihydrosphingosine, phytosphingosine, etc. The ceramides include N-acylated sphingosines, N-acylated phytosphingosines, N-acylated dihydrosphingosines, etc. obtained by synthesis or extraction from naturally occurring materials. An acyl substituent on sphingosine, dihydrosphingosine or phytosphingosine is a C8 to C22 linear or branched alkyl or alkenyl group, and 1 to 5 hydrogen atoms thereof may be substituted with hydroxyl groups. For example, it is possible to use not only ceramide 1, ceramide 2, ceramide 3, ceramide 1A, ceramide 6II, hydroxy caproyl phytosphingosine, but also synthetic pseudo-ceramides such as sphingolipid EX (JP-A 11-209248) and sphingolipid E (JP-B 01-042934). At least one kind of the sphingosines and ceramides can be used, and the content thereof is 0.01 to 5 percent by weight, more preferably 0.05 to 2 percent by weight, even more preferably 0.1 to 1 percent by weight, based on the total amount of the hair cosmetics.

The surfactant used in the present invention includes a cationic surfactant, a nonionic surfactant, an anionic surfactant and an amphoteric surfactant.

The cationic surfactant is preferably a compound represented by the following general formula (X):

wherein $R^{14}$ and $R^{15}$ each independently represents a hydrogen atom, a $C_1$ to $C_{28}$ alkyl group or a benzyl group, provided that they do not simultaneously represent hydrogen atoms or benzyl groups; and $An^-$ represents an anion.

When $R^{14}$ and $R^{15}$ each represents an alkyl group, preferred are those having 16 to 24 carbon atoms, more preferably 22 carbon atoms, even more preferably a linear alkyl group. The anion $An^-$ includes halide ions such as chloride ions and bromide ions, and organic anions such as ethyl sulfate ions and methyl carbonate ions, preferably halide ions, more preferably chloride ions. The cationic surfactant includes mono long chain quaternary ammonium salts, specifically behenyltrimethylammonium chloride, stearyltrimethylammonium chloride, cetyltrimethylammonium chloride and arachyltrimethylammonium chloride, among which behenyltrimethylammonium chloride is more preferable.

Examples of the nonionic surfactant include polyoxyalkylene sorbitan fatty esters, polyoxyalkylene sorbitol fatty esters, polyoxyalkylene glycerol fatty esters, polyoxyalkylene fatty esters, polyoxyalkylene alkyl ethers, polyoxyalkylene alkyl phenyl ethers, polyoxyalkylene (hydrogenated) castor oils, sucrose fatty esters, polyglycerol alkyl ethers, polyglycerol fatty esters, fatty acid alkanol amides and alkyl glycosides.

Among these nonionic surfactants, preferred are alkyl glycosides, polyoxyalkylene (C8 to C20) fatty esters, polyoxyethylene sorbitan fatty esters, polyoxyethylene hydrogenated castor oils and fatty acid alkanol amides. The fatty acid alkanol amides are preferably those containing an acyl group having 8 to 18 carbon atoms, more preferably 10 to 16 carbon atoms, and may be in the form of either a monoalkanol amide or a dialkanol amide. The fatty acid alkanol amides are more preferably those containing a hydroxyalkyl group having 2 to 3 carbon atoms. Specific examples of the fatty acid alkanol amides include oleic acid diethanol amide, palm kernel oil fatty acid diethanol amide, coconut oil fatty acid diethanol amide, lauric acid diethanol amide, polyoxyethylene coconut oil fatty acid monoethanol amide, coconut oil fatty acid monoethanol amide, lauric acid isopropanol amide and lauric acid monoethanol amide.

Examples of the anionic surfactant include those based on sulfates, sulfonates and carboxylates. Specific examples include polyoxyethylene alkyl ether sulfates, polyoxyethylene alkenyl ether sulfates, alkyl sulfates, polyoxyalkylene alkyl phenyl ether sulfates, alkyl sulfosuccinates, polyoxyalkylene alkylsulfosuccinates, alkane sulfonates, higher fatty acid salts, etc. Examples of the amphoteric surfactant include betaine-based surfactants. Among these, betaine-based surfactants such as betaine alkyldimethylaminoacetates and fatty acid amide propylbetaines are more preferable, and fatty acid amide propylbetaines are even more preferable. The fatty acid amide propylbetaines are preferably those containing an acyl group having 8 to 18 carbon atoms, more preferably 10 to 16 carbon atoms, even more preferably lauric acid amide propylbetaine, palm kernel oil fatty acid amide propylbetaine, and coconut oil fatty acid amide propylbetaine.

The content of the surfactant is preferably 0.05 to 20 percent by weight, more preferably 0.1 to 10 percent by weight, even more preferably 0.1 to 5 percent by weight, based on the total amount of the hair cosmetics.

In addition to the components described above, other components generally used in hair cosmetics can be incorporated into the hair cosmetics of the present invention. Specific examples include polymer compounds such as cationic cellulose, hydroxylated cellulose and highly polymerized polyethylene oxide; anti-dandruffs such as zinc pyrithione and benzalkonium chloride; pearling agents; extracts such as extract of Eucalyptus in a polar solvent; *Panax ginseng* extract, rice bran extract, fucoid extract, aloe extract, Alpinia leaf extract and chlorella extract; a liquid crystal forming agent; a chelating agent; an UV absorber; an antioxidant; a preservative; a coloring agent; a perfume, etc.

The hair cosmetics of the present invention can be used in the desired form of an aqueous solution, an ethanol solution, an emulsion, a suspension, gel, liquid crystals, aerosol, etc.

The hair cosmetics of the present invention can be used in a hair rinse, a hair conditioner, a hair treatment, a hair pack, a hair cream, a leave-on-treatment, etc. The hair cosmetics of the present invention can be produced in a usual manner.

EXAMPLES

The present invention is described in more detail by reference to the Examples. The Examples illustrate the present invention and are not intended to limit the present invention.

Hereinafter, the term "%" refers to % by weight.

Production Example 1

Preparation Example of Amideamine (I)

Behenic acid (LUNAC BA, manufactured by Kao Corporation) and dimethyl aminopropylamine were subjected as starting materials to amidation reaction to give behenic acid dimethylaminopropylamide. The purity was 98%, and other components include unreacted behenic acid, unreacted amine, water, etc. The composition of the fatty acid residue ($R^4CO$) was $C_{17}H_{35}CO/C_{19}H_{39}CO/C_{21}H_{43}CO/C_{23}H_{47}CO=1\%/9\%/88\%/2\%$.

Examples 1 to 8 and Comparative Example 1 to 3

Hair cosmetics (hair conditioners) having the compositions shown in Table 1 were prepared by the following method, then measured for their viscosity by the following method, evaluated sensorily by the following method, and measured for the degree of repaired cavities in the hair by the following method. The results are shown in Table 1.

<Preparation Method>

(1) The component (b) is added to purified water heated at 60° C. (aqueous phase).

(2) The component (a), the component (c) and other components are mixed and melted at 70° C. (oil phase).

(3) The oil phase in (2) is added to the aqueous phase while stirring with a propeller (about 250 rpm in production of about 1 L) and then emulsified while stirring for about 30 minutes.

<Method for Measuring Viscosity>

Viscosity was measured at 30° C. by Viscometer TV-10 manufactured by Toki Sangyo Co., Ltd.

<Sensory Evaluation Method>

A bundle of hair (20 g, 20 cm, Japanese female hair once permed) was washed with 3 g of shampoo. This shampoo composition contained 15% sodium polyoxyethylene alkyl (C12) ether sulfate (number of ethylene oxide units on average: 2.5) and 3% diethanol amide, the balance being water. Thereafter, 2 g of the prepared hair conditioner was applied to the hair, and the hair was rinsed for about 30 seconds with running water at about 40° C., and then evaluated for smoothness after application to the hair until rinsing (during wetting). Then, the hair was dried with a towel and dried with a dryer, and after drying, the hair was evaluated for smoothness, manageability, and luster. The evaluation was carried out by a panel of 8 persons and ranked under the following criteria:

Evaluation Criteria

A: Reported to be effective by 7 or more persons.

B: Reported to be effective by 5 to 6 persons.

C: Reported to be effective by 3 to 4 persons.

D: Reported to be effective by 2 or less persons.

<Degree of Repaired Cavities in the Hair>

0.5 g bundle of hair damaged by hair coloring was washed with 1 g of the above-mentioned shampoo. After water was slightly removed from the hair, 1 g of the prepared hair conditioner was applied onto the hair and then left for 1 minute, and 4 g of the hair conditioner was additionally applied onto the hair and left at 35° C. for 15 minutes. Then, the hair was rinsed for 15 seconds with running water, then dried with a towel and dried with hot air with a dryer for 1 minute. The above treatment of the hair corresponds to ordinary successive use of the hair conditioner for 1 week. This treatment was carried out repeatedly 4 times in total.

Using a simplified stereoscopic microscope (WIDE STAND MICRO, manufactured by PEAK, 10 times of magnification), the hair was irradiated with light in an oblique direction relative to the root of the hair (at an angle of 15 to 600 between the hair axis and the light illumination axis) and observed in the same plane as in the hair axis and the light illumination axis, and in a direction perpendicular to the hair axis. By this method, specular light on the hair surface, disturbing observation, can be eliminated, and the hair in which cavities were formed is observed in the form of whitish streak in only a porous structure of the medulla portion in the center of hair (FRAGRANSE JOURNAL, June, page 11, 2000). Before and after the treatment of hair, the full length of the porous portion is measured to determine the degree of repaired cavities according to the following equation:

Degree of repaired cavities (%)=[(full length of the porous portion (before treatment)−full length of the porous portion (after treatment))/full length of the porous portion (before treatment)]×100

TABLE 1

|  |  |  | Example 1 | Example 2 | Example 3 | Example 4 | Example 5 | Example 6 | Example 7 | Example 8 | Comparative example 1 | Comparative example 2 | Comparative example 3 |
|---|---|---|---|---|---|---|---|---|---|---|---|---|---|
| Hair cosmetics (%) | (a) | Behenic acid dimethylaminopropylamide | 1.8 | 1.8 | 1.8 | 1.2 | 1.8 | 1.8 | 0.25 | 0.25 | 1.8 | | 1.2 |
| | | Arachidic acid dimethylaminopropylamide | 0.1 | 0.1 | 0.1 | 0.1 | 0.1 | 0.1 | | | 0.1 | | |
| | | Stearic acid dimethylaminopropylamide | 0.1 | 0.1 | 0.1 | 0.7 | 0.1 | 0.1 | | | 0.1 | 2.0 | 0.8 |
| | (b) | Lactic acid | 0.7 | 1.5 | 2.5 | 1.5 | 1.3 | 1.3 | 1.5 | 1.5 | 0.4 | 1.5 | 0.4 |
| | | Glycolic acid | | | | | 0.5 | | | | | | |
| | | Malic acid | | | | | | 0.2 | | | | | |
| | (c) | Stearyl alcohol | 6 | 6 | 6 | 6 | 6 | 5 | 6 | 5 | 6 | 6 | 6 |
| | | Behenyl alcohol | | | | | | 1 | | 1 | | | |
| | | Stearoxypropyl dimethylamine* | | | | | | | 1.75 | 1.75 | | | |
| | Others | Benzyloxyethanol | 0.4 | 0.4 | 0.4 | 0.4 | 0.3 | 0.3 | 0.4 | 0.2 | 0.4 | 0.4 | 0.4 |
| | | Benzyl alcohol | | | | | | 0.1 | | 0.1 | | | |
| | | Phenoxyethanol | | | | | 0.1 | | | | | | |
| | | glycerine | | | | | | | | 0.2 | | | |
| | | Dipropylene glycol | 2 | 2 | 2 | 2 | 2 | 2 | 2 | 2 | 2 | 2 | 2 |
| | | Ion exchanged water | balance | balance | balance | balance | balance | balance | balance | balance | balance | balance | balance |
| Molar ratio of component (b) to the amine equivalent of component (a) | | | 1.5 | 3.1 | 5.2 | 2.8 | 3.7 | 2.9 | 3.0 | 3.0 | 0.8 | 2.8 | 0.9 |
| pH (5% aqueous solution) | | | 3.9 | 3.3 | 3.1 | 3.3 | 3.3 | 3.4 | 3.3 | 3.2 | 4.9 | 3.4 | 4.9 |
| Viscosity (30° C.) (mPa·s) | | | 10730 | 6600 | 6430 | 5800 | 6310 | 10940 | 10300 | 10000 | 15000 | 4000 | 13400 |
| Results of evaluation | During wetting | Smoothness | A | A | A | B | A | B | A | A | B | C | B |
| | After drying | Smoothness | A | A | A | A | A | A | A | A | A | C | A |
| | | Manageability | A | A | A | B | A | A | A | A | B | B | B |
| | | Luster | B | A | A | B | A | A | A | A | C | B | C |
| | Degree of repaired cavities in the hair (%) | | 65 | 75 | 80 | 65 | 75 | 75 | 70 | 75 | 10 | 65 | 10 |

*The effective content of stearoxy propyldimethylamine is 90 wt %, the balance (10%) being stearyl alcohol.

Example 9

A hair conditioner having the following composition was prepared.

| <Conditioner composition> | |
|---|---|
| Amideamine (I) in Production Example 1 | 1.8% |
| Stearyl alcohol | 6.0% |
| Benzyloxyethanol | 0.7% |
| Dimethylpolysiloxane (polymerization degree: 600) | 1.0% |
| Highly polymerized dimethylpolysiloxane (polymerisation degree 2600) | 1.2% |
| Decamethylcyclopentasiloxane | 1.5% |
| Amino-modified silicone-polyoxyalkylene block copolymer*[1] | 0.2% |
| Amino-modified silicone*[2] | 0.2% |
| Lactic acid | 2.1% |
| Glycolic acid | 0.2% |
| Dipentaerythritol fatty acid ester*[3] | 0.2% |
| Hydroxyethyl cellulose*[4] | 0.3% |
| Perfume, methylparaben | q.s. |
| Purified water (pH 3.2) | Balance |

*[1]FZ-3789 manufactured by Nippon Unicar Company Limited
*[2]SM-8704C manufactured by Dow Corning Toray Silicone Co., Ltd.
*[3]Cosmol 168AR manufactured by Nisshin Oil Mills, Ltd.
*[4]SE-850K manufactured by Daicel Chemical Industries, Ltd.

This hair conditioner was excellent in rich feeling, softness and smoothness of hair upon treatment (during wetting) and in softness, smoothness, manageability, and luster of hair after drying.

Example 10

A treatment agent having the following composition was prepared.

| <Treatment agent composition> | |
|---|---|
| Amideamine (I) in Production Example 1 | 2.0% |
| Behenyltrimethylammonium chloride | 0.3% |
| Stearyl alcohol | 6.5% |
| Behenyl alcohol | 1.5% |
| Isononyl isononanoate | 0.5% |
| Dimethylpolysiloxane (polymerization degree: 600) | 2.5% |
| Highly polymerized dimethylpolysiloxane (polymerization degree 2600) | 1.5% |
| Amino-modified silicone*[2] | 1.0% |
| Lactic acid | 0.5% |
| Glycolic acid | 1.5% |
| Malic acid | 0.1% |
| Dipropylene glycol | 3.0% |
| Benzyl alcohol | 0.2% |
| Benzyloxyethanol | 1.5% |
| Arginine*[5] | 0.2% |
| Pantothenyl ethyl ether | 0.1% |
| Perfume, methylparaben | q.s. |

-continued

<Treatment agent composition>

| | |
|---|---|
| Purified water (pH 3.2) | Balance |

*[5]L-arginine manufactured by Kawaken Fine Chemicals

This hair treatment agent was excellent in rich feeling, softness and smoothness of hair upon treatment (during wetting) and in softness, smoothness, manageability, and luster of hair after drying.

Example 11

<Conditioner composition>

| | |
|---|---|
| Amideamine (I) in Production Example 1 | 1.0% |
| Stearoxypropyldimethylamine*[1] | 1.2% |
| Stearyl alcohol | 5.5% |
| Benzyl alcohol | 0.5% |
| Dimethylpolysiloxane (polymerization degree: 600) | 1.0% |
| Highly polymerized dimethylpolysiloxane (polymerization degree 2600) | 1.2% |
| Decamethylcyclopentasiloxane | 1.0% |
| Amino-modified silicone-polyoxyalkylene block copolymer*[2] | 0.2% |
| Amino-modified silicone*[3] | 0.5% |
| Lactic acid | 2.2% |
| Dipentaerythritol fatty ester*[4] | 0.2% |
| Hybrid sunflower oil | 0.1% |
| Hydroxyethylcellulose*[5] | 0.3% |
| Highly polymerized polyethylene glycol*[6] | 0.1% |
| Perfume, methylparaben | q.s. |
| Purified water (pH 3.2) | Balance |

*[1]Composition: 90% stearoxypropyldimethylamine and 10% stearyl alcohol
*[2]SS-3588 manufactured by Dow Corning Toray Silicone Co., Ltd.
*[3]SM-8704C manufactured by Dow Corning Toray Silicone Co., Ltd.
*[4]Cosmol 168AR manufactured by Nisshin Oil Mills, Ltd.
*[5]SE-850K manufactured by Daicel Chemical Industries, Ltd.
*[6]POLYOX(™) WSR N-60K manufactured by The Dow Chemical Company

The invention claimed is:

1. Hair cosmetics comprising the following components (a), (b), (c) and (d): (a) an amideamine represented by the general formula (I):

$$R^1-\underset{\underset{O}{\|}}{C}-\underset{\underset{}{H}}{N}-(CH_2)_3-N\underset{CH_3}{\overset{CH_3}{\diagup}} \quad (I)$$

wherein $R^1CO$ represents fatty acid residues among which C20 or more fatty acid residues account for 75 percent by weight or more, C20 fatty acid residues account for 4 percent by weight or more, and C22 fatty acid residues account for 55 to 95 percent by weight,
(b) an organic acid, and
(c) a C8 to C30 aliphatic alcohol, and
(d) an organic solvent selected from the group consisting of (d2) to (d5):
(d2) N-Alkylpyrrolidones having a C1-18 alkyl group bound to a nitrogen atom,
(d3) Alkylene carbonates whose alkylene group has 2 to 4 carbon atoms,
(d4) Polypropylene glycols having a molecular weight of from 200 to 5000, and
(d5) Lactones or cyclic ketones represented by the general formula (III), (IV) or (V):

$$(R^5)_s\underset{(R^6)_t}{\diagdown}\overset{X}{\diagup}\diagdown_O \quad (III)$$

$$(R^5)_s\underset{(R^6)_t}{\diagdown}\overset{X}{\diagup}\diagdown_O \quad (IV)$$

$$(R^5)_s\underset{(R^6)_t}{\diagdown}\overset{X}{\diagup}\diagdown_O \quad (V)$$

wherein X represents a methylene group or an oxygen atom, $R^5$ and $R^6$ represent substituents which are different from each other, and s and t each represents 0 or 1
wherein the content of the component (b) is 1.5 to 10 times as many moles as the amine equivalent of the component (a).

2. The hair cosmetics according to claim 1, wherein the content of the component (c) in the hair cosmetics is 0.1 to 20 percent by weight.

3. The hair cosmetics according to claim 1 or 2, wherein the organic acid as component (b) is a hydroxycarboxylic acid or a dicarboxylic acid.

4. The hair cosmetics according to any of claims 1 to 2, which further comprise an ether amine represented by the general formula (XI):

$$R^{21}-O-(CH_2)_3-N\underset{R^{23}}{\overset{R^{22}}{\diagup}} \quad (XI)$$

wherein $R^{21}$ is a linear or branched C6 to C24 alkyl or alkenyl group, $R^{22}$ and $R^{23}$ are the same or different from each other and each represents a C1 to C6 alkyl group, or a group $-(AO)_mH$ in which A represents a C2 to C4 alkylene group, m is a number of 1 to 6, and the group A I number of m may be the same or different form one another and may be arranged in any order.

5. The hair cosmetics according to claim 1, wherein C20 or more fatty acid residues account for 75 percent by weight or more of said fatty acid residues.

6. The hair cosmetics according to claim 1, wherein C20 or more fatty acid residues account for 90 percent by weight or more of said fatty acid residues.

7. The hair cosmetics according to claim 1, wherein C20 fatty acid residues account for 4 percent by weight or more of said fatty acid residues.

8. The hair cosmetics according to claim 1, wherein C20 fatty acid residues account for 5 percent by weight or more of said fatty acid residues.

9. The hair cosmetics according to claim 1, wherein C22 fatty acid residues account for 55 to 95 percent by weight of said fatty acid residues.

10. The hair cosmetics according to claim 1, wherein C22 fatty acid residues account for 70 to 95 percent by weight of said fatty acid residues.

11. The hair cosmetics according to claim 1, wherein C22 fatty acid residues account for 80 to 95 percent by weight of said fatty acid residues.

12. The hair cosmetics according to claim 1, wherein the content of the component (a) in said hair cosmetics is from 0.1 to 10 percent by weight.

13. The hair cosmetics according to claim 1, wherein the content of the component (a) in said hair cosmetics is from 0.1 to 5 percent by weight.

14. The hair cosmetics according to claim 1, wherein the content of the component (a) in said hair cosmetics is from 0.5 to 3 percent by weight.

15. The hair cosmetics according to claim 1, wherein the content of the component (c) in said hair cosmetics is from 0.5 to 10 percent by weight.

16. The hair cosmetics according to claim 1, wherein a pH of said hair cosmetics in the form of a 5 percent by weight aqueous solution at 25° C. is from 2 to 8.

17. The hair cosmetics according to claim 1, wherein a pH of said hair cosmetics in the form of a 5 percent by weight aqueous solution at 25° C. is from 25 to 4.5.

18. The hair cosmetics according to claim 4, wherein the content of said ether amine in said hair cosmetics is from 0.01 to 20 percent by weight.

19. The hair cosmetics according to claim 4, wherein a weight ratio of component (a) to said ether amine is from 10/1 to 1/10.

20. The hair cosmetics according to claim 1, wherein a content of said organic solvent in said hair cosmetics is from 0.1 to 20 percent by weight.

* * * * *